(12) United States Patent
Schlottig et al.

(10) Patent No.: US 8,671,572 B2
(45) Date of Patent: Mar. 18, 2014

(54) METHOD FOR THE PRODUCTION OF A DENTAL IMPLANT

(75) Inventors: Falko Schlottig, Fullinsdorf (CH); Luis Alfonso Ortega Cruz, Selzach (CH)

(73) Assignee: Thommen Medical AG, Waldenburg (CH)

( * ) Notice: Subject to any disclaimer, the term of this patent is extended or adjusted under 35 U.S.C. 154(b) by 652 days.

(21) Appl. No.: 12/517,202

(22) PCT Filed: Dec. 17, 2007

(86) PCT No.: PCT/CH2007/000638
§ 371 (c)(1),
(2), (4) Date: Jun. 2, 2009

(87) PCT Pub. No.: WO2008/077263
PCT Pub. Date: Jul. 3, 2008

(65) Prior Publication Data
US 2010/0081109 A1     Apr. 1, 2010

(30) Foreign Application Priority Data
Dec. 22, 2006   (CH) ..................... 2102/06

(51) Int. Cl.
*B22F 3/14*    (2006.01)
*B22F 3/24*    (2006.01)
*B22F 3/26*    (2006.01)

(52) U.S. Cl.
USPC ........... 29/896.11; 419/2; 419/42; 433/201.1; 433/221

(58) Field of Classification Search
USPC ........... 29/896.11; 419/2, 42; 433/201.1, 215, 433/221; 264/16–20, 337, 338; 249/54, 249/114.1
See application file for complete search history.

(56) References Cited

U.S. PATENT DOCUMENTS

| | | | | |
|---|---|---|---|---|
| 2,196,875 A | * | 4/1940 | Sandler et al. | 75/228 |
| 3,145,102 A | * | 8/1964 | Simonich | 419/56 |
| 3,166,615 A | * | 1/1965 | Farrell | 264/413 |
| 3,421,972 A | * | 1/1969 | Cromwell et al. | 428/551 |

(Continued)

FOREIGN PATENT DOCUMENTS

| | | |
|---|---|---|
| DE | 129 195 A1 | 1/1978 |
| DE | 195 30 981 A1 | 2/1997 |

(Continued)

OTHER PUBLICATIONS

Translation of German Patent Document DE 102006005034A1 for Espacenet.com. Translation recived Apr. 16, 2012.*

(Continued)

*Primary Examiner* — David Bryant
*Assistant Examiner* — Jason L Vaughan
(74) *Attorney, Agent, or Firm* — Sughrue Mion, PLLC

(57) ABSTRACT

The invention discloses a novel implant provided with a macroporous surface on the top surface, and a method for the production of such a metallic and/or ceramic implant having a textured, particularly porous, surface for the at least partial insertion in hard tissue, such as in a bone, and/or into soft tissue. The implant is produced as a green compact, at least in sections, using a cold isostatic pressing, casting, and/or injecting (CIM, MIM) with subsequent sintering to obtain an implant, and is particularly characterized in that the surface is modified and/or prepared before sintering such that a macroporous surface is present after sintering without requiring any finishing.

28 Claims, 11 Drawing Sheets

(56) References Cited

U.S. PATENT DOCUMENTS

Figure 1:
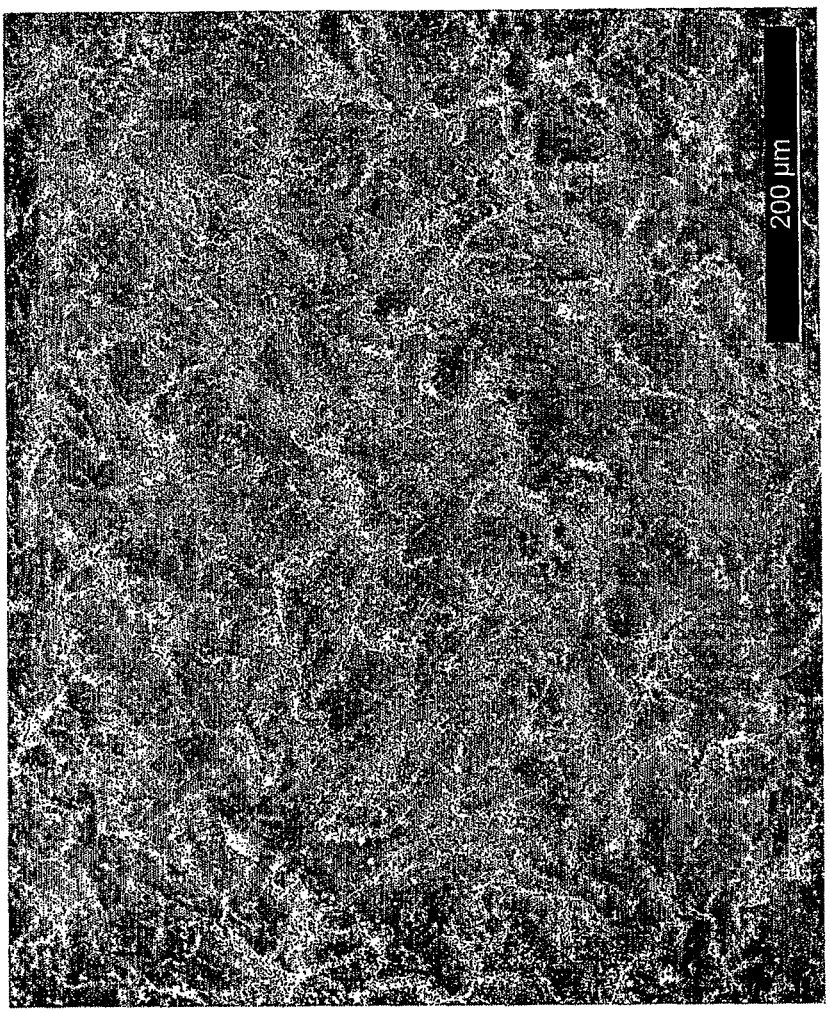

| | | | | |
|---|---|---|---|---|
| 3,674,512 | A | * | 7/1972 | Andros .................. 426/130 |
| 3,804,617 | A | * | 4/1974 | Conklin .................. 419/9 |
| 3,808,606 | A | * | 5/1974 | Tronzo .................. 428/613 |
| 4,259,072 | A | * | 3/1981 | Hirabayashi et al. ......... 433/173 |
| 4,261,745 | A | * | 4/1981 | Watanabe et al. ........... 419/8 |
| 4,430,061 | A | * | 2/1984 | Webb et al. ............... 433/9 |
| 4,954,080 | A | * | 9/1990 | Kelly et al. ............... 433/8 |
| 4,956,200 | A | * | 9/1990 | Malkowski ............... 427/133 |
| 4,983,355 | A | * | 1/1991 | Alfons .................... 264/645 |
| 5,246,530 | A | | 9/1993 | Bugle et al. |
| 5,251,468 | A | | 10/1993 | Lin et al. |
| 5,336,465 | A | * | 8/1994 | Matsunaga et al. .......... 419/2 |
| 5,342,201 | A | * | 8/1994 | Oden ..................... 433/223 |
| 5,480,301 | A | * | 1/1996 | Farzin-Nia et al. .......... 433/9 |
| 5,765,095 | A | * | 6/1998 | Flak et al. ................. 419/8 |
| 5,788,498 | A | | 8/1998 | Wohlwend |
| 5,910,007 | A | * | 6/1999 | Shimodaira et al. .......... 433/17 |
| 5,937,265 | A | * | 8/1999 | Pratt et al. ................. 419/6 |
| 6,022,509 | A | * | 2/2000 | Matthews et al. ........... 419/38 |
| 6,042,780 | A | * | 3/2000 | Huang .................... 419/36 |
| 6,168,633 | B1 | * | 1/2001 | Shoher et al. .............. 623/23.6 |
| 6,193,761 | B1 | * | 2/2001 | Treacy .................... 623/23.55 |
| 6,210,612 | B1 | | 4/2001 | Pickrell et al. |
| 6,264,469 | B1 | * | 7/2001 | Moschik ................... 433/8 |
| 6,488,503 | B1 | * | 12/2002 | Lichkus et al. ............. 433/202.1 |
| 6,502,442 | B2 | * | 1/2003 | Arola et al. ............... 72/53 |
| 6,849,230 | B1 | | 2/2005 | Feichtinger |
| 6,994,550 | B2 | * | 2/2006 | Knapp et al. .............. 433/207 |
| 7,011,522 | B2 | * | 3/2006 | Panzera et al. ............. 433/215 |
| 7,074,479 | B2 | | 7/2006 | Rogowski et al. |
| 7,763,204 | B2 | * | 7/2010 | Voice et al. ............... 264/604 |
| 8,048,345 | B2 | * | 11/2011 | Feith ...................... 264/19 |
| 2001/0046608 | A1 | | 11/2001 | Pickrell et al. |
| 2003/0180518 | A1 | | 9/2003 | Rogowski et al. |
| 2004/0038180 | A1 | | 2/2004 | Mayer et al. |
| 2004/0121291 | A1 | * | 6/2004 | Knapp et al. .............. 433/218 |
| 2004/0210309 | A1 | | 10/2004 | Denzer et al. |
| 2005/0064007 | A1 | | 3/2005 | Steinemann et al. |
| 2005/0106534 | A1 | | 5/2005 | Gahlert |
| 2005/0266380 | A1 | | 12/2005 | Soler et al. |
| 2006/0084035 | A1 | | 4/2006 | Volz |
| 2006/0105297 | A1 | * | 5/2006 | Knapp et al. .............. 433/206 |
| 2006/0163774 | A1 | * | 7/2006 | Abels et al. ............... 264/293 |
| 2006/0168815 | A1 | * | 8/2006 | Saliger et al. ............. 29/896.11 |
| 2006/0185170 | A1 | * | 8/2006 | Lewis et al. ............... 29/896.11 |
| 2006/0246399 | A1 | | 11/2006 | Ehrl |
| 2007/0202466 | A1 | | 8/2007 | Schwarz et al. |
| 2008/0057475 | A1 | | 3/2008 | Feith |

FOREIGN PATENT DOCUMENTS

| | | | | |
|---|---|---|---|---|
| DE | 196 38 927 | A1 | 3/1998 | |
| DE | 197 26 961 | C1 | 11/1998 | |
| DE | 102 43 101 | A1 | 1/2004 | |
| DE | 20 2004 020 338 | U1 | 5/2005 | |
| DE | 10 2005 005 656 | A1 | 1/2006 | |
| DE | 102006005034 | A1 * | 3/2006 | ............ A61L 27/00 |
| DE | 10 2005 013 200 | A1 | 9/2006 | |
| DE | 10 2006 036 039 | A1 | 2/2008 | |
| EP | 0 388 576 | A1 | 9/1990 | |
| EP | 1 570 804 | A1 | 9/2005 | |
| EP | 1 825 830 | A1 | 8/2007 | |
| FR | 2 721 196 | A1 | 12/1995 | |
| WO | 98/43927 | A1 | 10/1998 | |
| WO | 01/19556 | A1 | 3/2001 | |
| WO | 01/72664 | A1 | 10/2001 | |
| WO | 03/045268 | A1 | 6/2003 | |
| WO | 03/059407 | A1 | 7/2003 | |
| WO | 2004/096075 | A1 | 11/2004 | |
| WO | 2007/090529 | A1 | 8/2007 | |
| WO | 2008/009272 | A1 | 1/2008 | |

OTHER PUBLICATIONS

Roche Lexikon Medizin, Urban & Fischer (Hrsg.), Impressum, 2003, 5. Aufl.

D. M. Brunette, et al., "Titanium in Medicine, Material Science, Surface Science, Engineering, Biological Responses and Medical Applications", Engineering Materials, Springer.

Marion L. Maroney, "A Guide to Metal and Plastic Finishing", 1991.

R. K. Pandey, et al., "Handbook of Semiconductor Electrodeposition", Applied Physics, 5, 1996.

George J. Rudzki, "Surface Finishing Systems: Metal and Non-Metal Finishing Handbook-Guide", 1983, American Society for Metals, Metals Park, Ohio, U.S.A, Finishing Publications Ltd., Teddington, Middlesex, England.

M. J. O'Keefe, et al., "The Science, Technology and Materials Applications of Physic Vapor Deposition Processes", Materials and Processes for Surface and Interface Engineering (NATO Asi Series), Series E, Applied Sciences, 115, Pauleau, 1995, Ives (Editor).

* cited by examiner

METHOD FOR THE PRODUCTION OF A DENTAL IMPLANT

TECHNICAL FIELD

The present invention concerns an implant, especially a dental implant having a porous surface for the at least partial insertion into a bone, which has improved osteointegration characteristics. The implant therein is ceramic, but can also be metallic. Furthermore, the present invention concerns a method for the production of such an implant as well as uses of such an implant.

BACKGROUND OF THE INVENTION

Injured or damaged parts of the hard- and/or soft tissue of the human body are restored the best by using autologous hard- and/or soft tissue. This is not always possible for various reasons, which is why in many cases synthetic material is used as a temporary (biodegradable or post-operatively removable, respectively) or permanent replacement material.

Implants which are anchored in hard- and/or soft tissue, serve the temporary or permanent replacement or the support of parts of the musculoskeletal system which have been damaged by accident, use, deficiency or disease, or which have been otherwise degenerated, including especially parts of the chewing apparatus. A synthetic, chemically stable material, which is introduced into the body as a plastic replacement or for mechanical enforcement is normally called an implant (see e.g. Roche Lexikon Medizin, Urban & Fischer (Pubis.); $5^{th}$ edition 2003). The support- and replacement function in the body is taken over on the basis of the mechanical features and the implant design. Hence, for instance hip- and knee joint prostheses, spine implants and dental implants have been clinically used successfully for many years.

For the anchoring of the implant and the compatibility of the implant at the interface between the implant surface/neighboring tissue, the implant surface has a great significance. Hence, measurements have shown that, almost independently of the basic material used, implants with a smooth surface are anchored only poorly in the bone (poor osteointegration), while implants with a structured surface enter into a good mechanical- and, in case of a corresponding design of the surface, also a good biological connection with the surrounding hard- or soft tissue (see e.g. Titanium in Medicine, Material Science, Surface Science, Engineering, Biological Responses and Medical Applications Series: Engineering Materials, Brunette, D. M.; Tengvall, P.; Textor, M.; Thomsen, P. (Eds.)).

The time necessary for a sufficient ingrowth, which is an important and central feature for implants, is termed osteointegration time, or, in the dental field also osseointegration time, respectively. Thereby, the time is described, which passes by until the bone substance has connected with sufficient force and durably with the implant surface, so to speak, until it has virtually integrated into the implant surface.

Various methods are used for surface treatment and surface structuring, see e.g. A Guide to Metal and Plastic Finishing (Maroney, Marion L.; 1991); Handbook of Semiconductor Electrodeposition (Applied Physics, 5) (Pandey, R. K., et al.; 1996); Surface Finishing Systems: Metal and Non-Metal Finishing Handbook-Guide (Rudzki, George J.; 1984); Titanium in Medicine, Material Science, Surface Science, Engineering, Biological Responses and Medical Applications Series: Engineering Materials, (Brunette, D. M.; Tengvall, P.; Textor, M.; Thomsen, P. (Eds.)); and Materials and Processes for Surface and Interface Engineering (NATO Asi Series. Series E, Applied Sciences, 115, Pauleau, Ives (Editor); 1995); and the references cited therein.

Implants nowadays are produced of various materials, such as for example of titanium, niobium, zirconium, tantalum, of alloys such as e.g. titanium alloys, implant steel, of CoCr alloys, of various polymers and ceramics e.g. on the basis of zirconium oxides, aluminium oxides, titanium oxides, etc.

Besides the mechanical methods of treatment, implants for example can also be produced by a combination of casting and sintering. These methods are known for metal as MIM (Metal Powder Injection Molding) and for ceramics as CIM (Ceramic Injection Molding), such as e.g. from US 2004/0038180.

For the production of dental implants, both methods can also be coupled, as is described in EP 1 570 804 A1. Furthermore, a combination with mechanical treatment of the implant produced by MIM or CIM is possible, such as for example is described in EP 1 570 804 A1, that, following sintering, the surface can be post-treated either by a blasting treatment or by chemical surface modification (e.g. acid etching).

For many implants, especially for dental implants, mainly titanium and its alloys are used, as these materials have a sufficiently low elasticity module and a relatively high stability. However, measurements have shown that titanium implants with a smooth surface structure are only insufficiently anchored in the bone, while implants with a roughened surface result in a noticeably improved bone implant connection with respect to the traction- and torsion resistance.

In EP 0 388 576 A1, it is thus suggested to apply in a first step a macro-roughness onto a metallic implant surface by sand blasting, and to subsequently overlay it with a micro-roughness by a treatment in an acid bath. Thereby, the implant surface can be roughened by sand blasting and subsequently treated with an etching agent, e.g. hydrofluoric acid or a hydrochloric acid/sulphuric acid mixture. By this structuring of the surface, a safe connection between hard tissue and metal is achieved.

In the area of dental implants, titanium, especially in the visible front oral area, is unsuitable for aesthetic reasons, as the material optically differs from the hard- and the visible soft tissue environment. It is therefore desirable to use a different material which doesn't show these disadvantages. Ceramic materials, such as zirconium oxide, titanium oxide or aluminum oxide or mixtures thereof, materials are available, which show an extremely high stability, especially, if the form bodies are compressed hot-isostatically or post-compacted hot-isostatically. A specific yttrium-stabilized zirconium oxide ceramic, which has about 92.1-93.5 weight-% $ZrO2$, 4.5-5.525 weight-% $Y2O3$ and 3.8-2.2 weight-% $HfO2$, is for example known from U.S. Pat. No. 6,165,925. Other prevalent ceramics are discussed in the introductory part of U.S. Pat. No. 6,165,925 extremely high stability, The use of ceramics, for example of a zirconium oxide ceramic, a titanium oxide ceramic, or an aluminium oxide ceramic, as a material for the production of an implant anchored in the hard- or soft tissue, is tedious, as it is necessary for a sufficient mechanical stability of the ceramic to be produced without measurable porosity, normally simultaneously resulting in a smooth, extremely hard surface.

For smooth ceramic surfaces, no direct and sufficiently mechanically stable connection with the surrounding hard tissue is to be expected. Therefore, implants of pure ceramics such as zirconium oxide, titanium oxide or aluminium oxide, or mixtures thereof, have hardly been used so far in the direct contact with hard tissue. For the anchoring in hard tissue, constructive connections with metallic implant materials are used, for example in hip prosthetics or in oral implantology.

For example, in DE 195 30 981 A1, a pre-fabricated fully ceramic implant construction of zirconium dioxide is described for the dental coloured design of artificial crown stubs carried by implants. The actual implant therein consists of surface-structured metallic titanium, the aesthetics of the visible part being displayed via a zirconium oxide ceramic.

In WO 2004/096075 A1, a dental implant of a one-piece base body is described, consisting of zirconium oxide or of a zirconium oxide/aluminium mixture. A surface treatment is not described, and it is questionable whether such an implant structure shows a sufficient osseointegration at all.

FR 2 721 196 A1 describes a one-piece implant based on zirconium oxide. For the improvement of the osteointegration, the corresponding implant part shall be provided with a coating, for example of hydroxyapatite.

In WO 03/045268 A1, a ceramic implant on the basis of zirconium oxide is described. The external surface of the anchoring part is at least partially either roughened by an erosive method, or micro-structured, or provided with a coating. Therein, after a blasting treatment, such as by sandblasting, also chemical methods, especially etching methods are taken into consideration, which can be applied partially supplementary as a post-treatment to a previous mechanical treatment. Especially preferred is first a blasting treatment, such as by sand-blasting with Al2O3, and subsequently an etching treatment, with phosphoric acid, sulphuric acid, hydrochloric acid, or mixtures thereof. Furthermore, the treated implant can be stored in a suitable fluid, for example de-ionized water, or in a NaCl-solution. Thereby it is avoided that the surface loses its activation completely or partially by components of the air prior to the insertion of the dental implant. This is how an osteointegration is supported.

The problem therein is, that with such a combined treatment, the depth of the roughness remains small due to the high hardness of the zirconium oxide ceramic, and that the ceramic is chemically extremely stable with respect to the treatment with phosphoric acid, sulphuric acid, hydrochloric acid, or mixtures thereof.

In DE 10 2005 013 200, a two-part ceramic implant is described, including a micro- and macro-structuring and the chemical or biochemical/pharmaceutical modification, respectively, of the surfaces or selected surfaces of the implant, respectively. A method for achieving this surface structure or the surface modification is not specifically described.

SUMMARY OF THE INVENTION

One of the underlying objects of the invention, among others, is therefore, to avoid the disadvantages of the state of the art, and to propose implants, which anchor quickly and lastingly in hard- and soft tissue and thus show a good osteointegration or osseointegration, respectively. Specifically therefore, an improved metallic and/or ceramic implant with a structured, especially porous surface for the at least partial insertion into hard tissue, such as into a bone, and/or into soft tissue shall be proposed. Furthermore, a suitable method for the production thereof shall be proposed.

Preferably, a dental implant is concerned. The method for production thus is especially preferably a production method for production of a dental implant.

Likewise, however, also implants outside the field of dental implants are concerned. The method for production thus alternatively is a method for the production of implants outside the field of dental implants.

It thus especially concerns a method for the production of a metallic and/or ceramic implant with a structured, especially porous surface for the at least partial insertion into hard tissue such as in a bone and/or in soft tissue, wherein the implant is produced at least area-wise by the aid of cold-isostatic compression, casting and/or injection molding (CIM, MIM) to a green body with subsequent sintering to an implant. Therein, the method is characterized in that prior to sintering, the surface is changed and/or prepared such that after sintering a macroporous surface is present without any additional post-treatment. However, this does not eliminate the possibility of an additional post-treatment, as far at it is still reasonable or necessary, for example it can be reasonable to subsequently add a chemical post-treatment for the creation of a micro-porosity.

Therein, a macroporous surface is understood in that a topography (topological structuring) and/or pores with an average size of more than 2 μm, preferably more than 5 μm, most preferably >20 μm is/are present.

During the production of an implant by a combination of casting and sintering, or by MIM or CIM, or a combination of both methods, respectively, so far no possibilities are known within this method for the production of a dental implant, to achieve a suitable roughness or porosity, respectively, on the surface of the implant, in the state of the art only methods are to be found, in which the modification of the surface is carried out in a step following the sintering.

With respect to the two methods CIM and MIM, reference is made for exemplary purposes to WO 97/38811 and U.S. Pat. No. 5,482,671, the contents of which is explicitly incorporated into the present disclosure with respect to the two methods.

Basically, in this method for production, one usually proceeds in that first a powder is provided as a starting material, for example as a mixture. Subsequently, the cold-isostatic compression, casting, and/or injection molding, take place, followed by a sintering process, in which the actual ceramic or the actual stable metallic composite, respectively, is formed. Thus, for the production, so-called green parts or green bodies are first formed of artificially produced raw materials. These green bodies normally contain, besides the ceramic or metallic powder mixtures, also moist and organic binding agents. Firstly, the green body is dried. Then normally all component parts, especially of the binding agent, which are volatile, vaporizing or burning at high temperatures, must be removed from the ceramic green body. After drying and burning out or debindering/coking, respectively, the structure of the green body is merely held together by adhesion forces and requires an especially careful handling during the further process steps. Finally, the burning or sintering of the ceramic takes place. In this step, the ceramic body obtains its stability.

According to a first preferred embodiment, the method is characterized in that the green body is modified after the cold-isostatic compression, casting and/or injection molding and prior to the final sintering by blasting of the surface of the green body.

According to a further preferred embodiment, the method is characterized in that an abrasive and/or surface densifying blasting agent is used as a blasting agent for the blasting. Especially preferably, a metallic blasting agent, such as steel balls, a ceramic blasting agent, such as $Al_2O_3$, $ZrO_2$, $SiO_2$, Ca-phosphates, $TiO_2$, $NaO_2$, CaO, MgO, an organic or natural blasting agent as nut shells or rice in various particle- and splitter sizes, or mixtures of said blasting agents is used. Alternatively, or in addition, the blasting agent for the blasting can be ice balls or ice particles, organic blasting agents such as stearates, waxes, paraffines, or preferably carbamide, melamine resin, biuret, melamine, ammonium carbonate and ammonium bicarbonate or mixtures thereof.

Preferably, blasting agents are used which can be removed without residues at temperatures up to max. 600° C. or max. 300° C., prior to the final sintering, wherein this removal preferably is carried out in an oxidizing or reducing or inert atmosphere, such as especially under $O_2$, $N_2$, $NH_4$, Ar or in vacuum. A preferred blasting agent in this respect is ammonium bicarbonate, which already sublimes from the surface of the green body at 65° C. and leaves behind the desired structure in the surface.

Typically, the particle size of the blasting agent lies in the ranges of 0.01-0.25 mm, preferably in the range of 10-200 μm, especially preferably in the range of 50-110 μm. Preferably, a blasting pressure in the range of 0.2-7 bar, preferably between 0.2-5 bar, especially preferably in the range of 0.8 bar is selected. Typically, the blasting treatment is carried out during a time period between 15 and 65 seconds, preferably between 35 and 55 seconds, especially preferably in the range of 50 seconds. Therein, it is shown to be advantageous, if the distance from the jet to the implant is selected in the range of 25-80 mm, especially between 25 and 60 mm, especially preferably in the range of 30 mm. It is generally advantageous to select a bore diameter of the jet in the range of 0.8-1.2 mm, preferably 0.8-1.0 mm. The use of a flat jet, i.e. a jet, the outlet of which in its cross-section is not circular, but elongated (rectangular, with or without rounded edges, oval, virtually oval), is especially preferred. The width of the jet opening therein is preferably at least 0.2 times larger than the height, with a possible width in the range of 1.2-1.4 mm and a possible height in the range of 0.6-1.0, preferably 0.8 mm.

According to a further preferred embodiment, a mixture of two blasting agents with different particle sizes is used as a blasting agent. Thereby, among others, a virtually bimodal distribution of the produced roughness can be ensured, in other words resulting in fine as well as rough structures. Different blasting agents in this context are to be understood as different with respect to the material of the blasting agent. It is for example possible to use a mixture of a first component part with a rough distribution of the particle size and a second component part with a fine average particle size of the same material as a blasting agent (explicitly bimodal distribution of one single material).

However, in addition to the different average particle size, a different material, such as for example an organic rough blasting agent and an anorganic fine blasting agent is preferred.

Preferably, the difference in the average particle size of the different blasting agents in the mixture lies in the range of a factor 5-10.

Thereby, for example a first blasting agent can be present in the mixture, which has an average particle size in the range of 0.1-0.2 mm, preferably in the range of 0.2-0.8 mm.

Preferably an organic blasting agent is used, for example of fruit kernels (for example peach pits and/or apricot pits).

Furthermore, a second blasting agent can be present in the mixture, having an average particle size in the range of 0.01-0.1 mm, preferably in the range of 0.03-0.9 mm, wherein it preferably is an anorganic blasting agent, especially on the basis of aluminium oxide (Al2O3).

Generally, the ratio of first to second blasting agent lies in the range of 5:1-1:5, preferably in the range of 3:1-1:1.

Furthermore, it is especially preferred that blasting takes place in at least two steps, wherein in one step the so-called mixture is used and in a subsequent step merely the blasting agent with the smaller particle size is used, preferably as an anorganic blasting agent, wherein preferably the second step is carried out at an at least 5-10 times lower pressure.

Preferably, during the step of using a mixture, a blasting pressure in the range of 2-7 bar, preferably 3-5 bar is used. Furthermore, in this step, the time of treatment is in the range of 15-65 seconds, preferably in the range of 25-45 seconds. Furthermore, the distance from the jet to the implant can lie in the range of 25-80 mm. Furthermore, the bore diameter of the jet can lie in the range of 1.2-2.0 mm.

Preferably, in a possibly present second step, a blasting pressure in the range of 0.2-0.8 bar, preferably in the range of 0.2-0.4 bar can be used. Furthermore, the time of treatment can be in the range of 10-35 seconds, preferably in the range of 15-25 seconds. Furthermore, the distance from the jet to the implant can lie in the range of 30-50 mm. Furthermore, the bore diameter of the jet can lie in the range of 0.8-1.2 mm.

As already mentioned, it is possible that the porous surface is at least area-wise further modified by an erosive chemical or physical treatment following the sintering.

In this context, for example an acid treatment is preferred, for example by the aid of concentrated sulphuric acid, and/or hydrochloric acid, and/or another strong acid at an increased temperature (for example 100° C.-300° C.) and over a time period of more than one minute.

In this context, however, it is also and especially preferred, that this subsequent treatment encompasses a molten salt modification, carried out at least area-wise, preferably, in that the implant is structured by etching at the surface by a molten salt, wherein especially preferably essentially exclusively an erosion of material takes place during the etching in the molten salt.

Especially in the context of the use of an anorganic blasting agent, especially if this is used as a fine blasting agent in a mixture, it is ensured by the subsequent treatment in the molten salt, that any blasting agent still present on the implant is removed. In other words, while the rough blasting agent is already removed during sintering, also the fine blasting agent, which typically is still present on the surface after sintering of the green body, can thereby be removed essentially without residues.

The molten salt can be a molten salt of alkali- and/or alkaline earth-nitrates, hydroxides or halogens, or a mixture of these salts. It is preferred that the molten salt is a molten salt with at least one hydroxide, especially with at least one alkali- and/or alkaline earth-hydroxide, or that the molten salt is a molten salt exclusively consisting of one or more hydroxides, especially of one or more alkali- and/or alkaline earth-hydroxides.

Therein, the molten salt can be a molten salt of potassium hydroxide, and/or sodium hydroxide, and/or lithium hydroxide.

The molten salt can also be a molten salt with at least one chloride, especially with at least one alkali- and/or alkaline earth-chloride, or the molten salt can be a molten salt exclusively consisting of one or more chlorides, especially of one or more alkali- and/or alkaline earth-chlorides.

Preferably, the molten salt for surface modification is a binary molten salt of potassium hydroxide and sodium hydroxide, or of potassium chloride and lithium chloride, preferably in a ratio of 2:1-0.5:1, preferably in the range of 1.5:1-0.75:1, especially preferably in the range of 1:1 or 7:5, wherein the process is preferably carried out at a temperature in the range of 100-600° C., especially in the range of 150-250° C.

In this treatment in a molten salt, the surface can be exposed to a molten salt at least area-wise for a time period of 10 minutes to 300 hours, preferably of at least 2 hours, preferably from 10 to 100 hours, especially from 25 to 35 hours.

Preferably, the implant consists of ceramic, however, it can also, as already mentioned, be of a metallic basis or can comprise a combination of these two materials.

The implant especially preferably is an implant containing zirconium oxide, to which possibly additionally is added yttrium oxide and hafnium oxide, and/or containing aluminium oxide, possibly additionally containing silicium dioxide, ferric (III) oxide, and/or sodium oxide, and/or containing silicium nitride, possibly additionally containing silicium dioxide, ferric (III) oxide and/or sodium oxide, and or containing titanium oxide and/or being formed of mixtures of said materials.

Alternatively or additionally, it is possible to carry out the method such that the green body is changed and/or prepared on its surface by a blasting agent during the cold-isostatic compression, casting, and/or injection molding by a modification of the surface of the cold-isostatic compression-, casting- or injection molding tool prior to compression, casting or injection molding of the starting material to a green body. It is also possible that the green body is changed and/or prepared prior to sintering at least on its surface during the cold-isostatic compression, casting and/or injection molding by addition of a filler material to the starting material. The modification of the tool surface with a filler can be carried out by the adherence of the filler to the tool surface. The temporary binding of the blasting agent or filler material, respectively, to the tool surface can be carried out with binders, for example organic binders such as for example PVA or also with waxes.

In both cases, these treatments are carried out such that the structure of the surface of the cold-isostatic compression-, casting- or injection molding tool is reproduced in the surface of the green body, or that the filler material removed subsequently prepares the surface, respectively.

Preferably, the filler material is selectively arranged only in the surface area, especially preferably in that in a first step starting material with filler material is supplied to the form (preferably such that it is arranged in the form in the future surface area of the implant), and subsequently in a second step starting material without filler material. Compared to methods, which in any case are only known from other fields, not from the field of production of implants (see for example DE 102 24 671 C1), in which a porosity is provided in the entire body by filler material in the entire mass, it is also preferred to design the implant in its core without such fillers, as otherwise a sufficient stability cannot be achieved in this core.

Preferably, the filler material are high-melting organic or anorganic compounds, low-melting metals, especially preferably carbamide ($CH_4N_2(H_2N-CO-NH_2)$), biuret ($C_2H_5N_3O_2$), melamine ($C_3H_6N_6$), melamine resin, ammonium carbonate (($NH_4)CO_3H_2O$) or ammonium bicarbonate ($NH_4HCO_3$) or mixtures thereof. With respect to possible materials as fillers, reference is made to the disclosure of DE 102 24 671 C1, which in this respect is explicitly included in the present disclosure.

Furthermore, the present invention concerns an implant, producible or produced by a method as described above.

In addition, the present invention concerns the use of such an implant as a dental implant, especially as a crown stub, as a threaded part, screw and/or pin.

Further preferred embodiments of the invention are described in the dependent claims.

This problem is solved in summary in that the structured or porous surface, respectively, is, at least area-wise during the CIM or MIM process, respectively, surface-modified on the green body, i.e. on the intermediate product after casting or injection molding and prior to the final sintering, or is the result of a surface-modification, respectively. The problem is solved by a specifically treated surface of the implant, thereby having specific properties, wherein the treatment can be carried out over the entire implant surface as well as on partial component parts of the implant surface.

Within the scope of this invention, mainly implants are concerned which are based on ceramic materials. However, it is likewise possible to structure implants on a metallic basis by the aid of the processes described below. Accordingly, it is also possible to provide a metallic implant, which has a structured or porous surface, respectively, which at least area-wise during the CIM or MIM process, respectively, is surface-modified on the so-called green body, i.e. on the intermediate product after the cold-isometric compression, casting, or injection molding, and prior to the final sintering, or is the result of a surface modification, respectively. Additionally, the optimization of the surface structure is possible by thermal heat treatments (debindering, sintering, HIP). All embodiments described below correspondingly were able to be used likewise on metallic materials, such as for example implants on the basis of titanium, zinc, niobium, tantalum, or corresponding alloys.

The core of the invention therefore consists in that it was surprisingly found that especially green bodies on the basis of ceramic (slip), but also of metal (slip) based green bodies can be thus modified on the surface prior to sintering, that they subsequently show excellent osteointegration or osseointegration, respectively. It can be shown that the osteointegration or osseointegration, respectively, of a surface thus modified is better than the corresponding values for acid-modified surfaces and/or surfaces especially of mechanically produced ceramics which were merely provided with a macro-roughness by sand blasting, or of ceramics which were produced by CIM and were provided with a macro-roughness by sand blasting after the final sintering.

The so-called green body thus is structured by blasting with various blasting agents prior to the final sintering or preferably prior to a heat treatment prior to the debindering on the surface. This for example can be carried out by a defined blasting process. Furthermore, the possibility exists, to apply the blasting agent to the casting- or injection molding tool prior to casting or injection molding or treat it therewith prior to casting or injection molding. Suitable blasting agents are all known abrasive or surface densifying or natural blasting agents, depending on the desired roughness or porosity of the surface. Therein, it is also found that the surfaces produced according to the invention may contain partially incorporated component parts of the blasting agents used. Advantageously, according to the invention, further blasting agents can be used which can be removed without residues prior to the final sintering. Such suitable blasting agents are for example the so-called organic blasting agents. These blasting agents can be removed without residues at temperatures up to max. 600° C. or max. 300° C. prior to the final sintering or preferably prior to a heat treatment before debindering. Therein, it is advantageous to carry out this treatment in an oxidizing or reducing or inert atmosphere. Ammonium bicarbonate is especially advantageous, which already sublimes from the surface of the green body at 65° C. and leaves behind the desired structure in the surface. The dimension or the particle size, respectively, of the blasting agents determines the dimension of the surface structuring. Typical particle sizes are in the ranges of 10-200 μm, preferably 50-110 μm. These blasting agents have a purely surface structuring effect, (the surface produced according to the invention thereby has no residues of the blasting agents). The resulting topological structure therein, in case of a corresponding setting of the conditions and a corresponding material selection, corresponds to a macro-roughness, in other words a roughness with a dimension of 1 μm to 50 μm, preferably 1 μm-10 μm.

This macro-structured surface can be additionally micro-structured, for example with a treatment in a molten salt, such as e.g. described in CH 01339/06.

Additional coatings, such as for example of apatite, are not necessary and preferably also not present.

The ceramic can be of various types, wherein these are known from the state of the art. For example, a ceramic can be used, which contains titanium oxide or zirconium oxide, which possibly additionally contains yttrium oxide and/or hafnium oxide. In this respect, see for example U.S. Pat. No. 6,165,925, the disclosure of which shall be explicitly encompassed by the disclosure of the present description with respect to the composition and the production of such ceramics on the basis of zirconium oxide.

Alternatively, it is possible to use ceramics, which contain aluminium oxide, to which possibly additionally silicium dioxide, ferric (III) oxide, and/or sodium oxide is added. It is furthermore possible to use a ceramic, which contains silicium nitride, to which possibly additionally silicium dioxide, ferric (III) oxide, and/or sodium oxide is added. Also ceramics based on mixtures or multi-layer systems on the basis of said materials are possible.

According to a preferred embodiment the implant is a dental implant, its surface which is exposed to the bone and/or soft tissue in an implanted state being at least area-wise macro-structured with the aid of the described process, and the macro structure possibly being underlaid with a micro structure, which for example is molten salt- or acid-modified.

SHORT DESCRIPTION OF THE FIGURES

Figure 2:
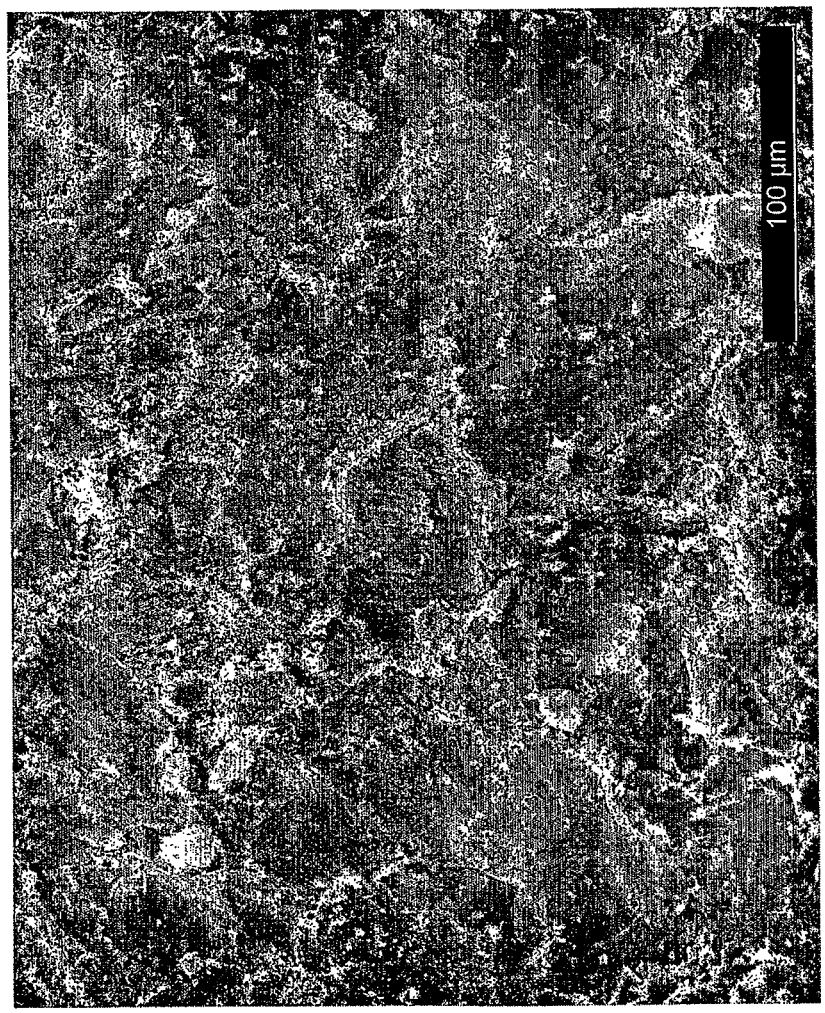
Figure 3:
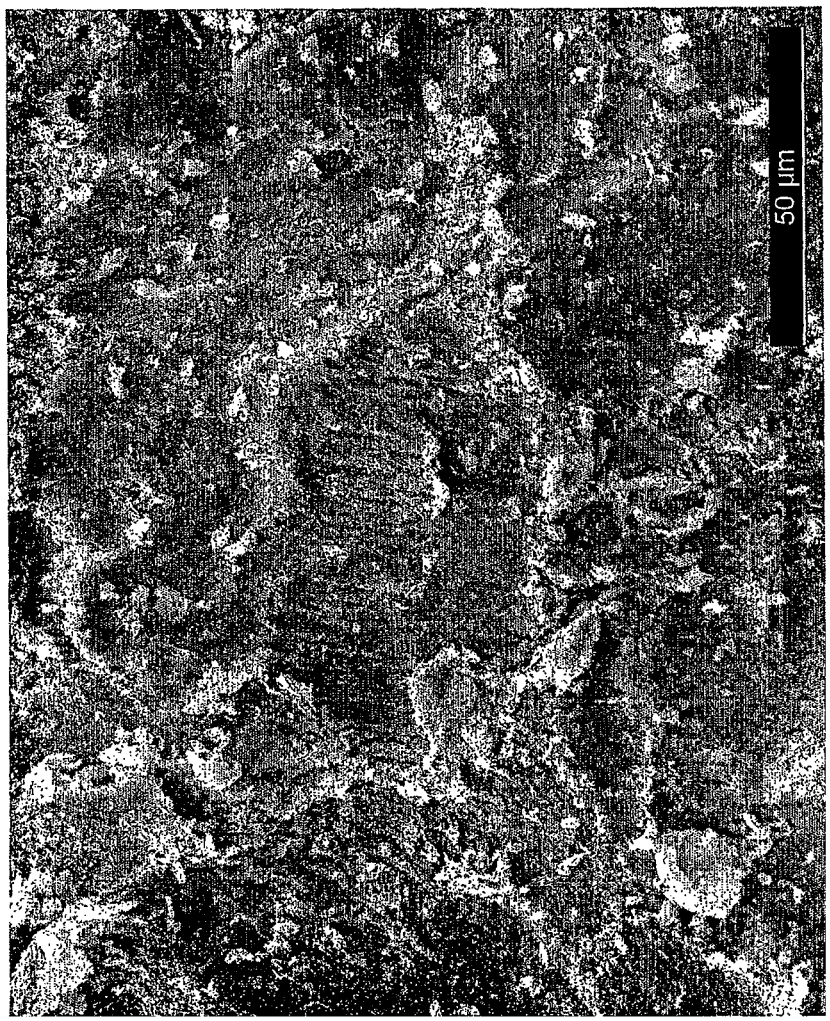
Figure 4:
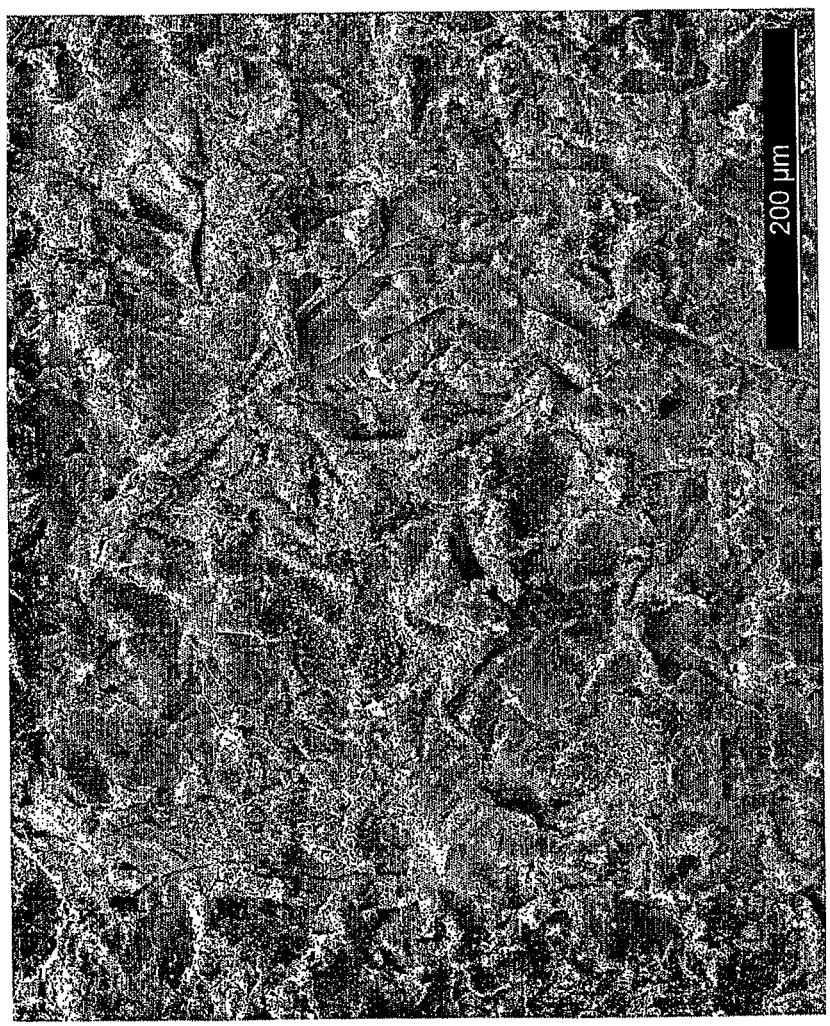
Figure 5:
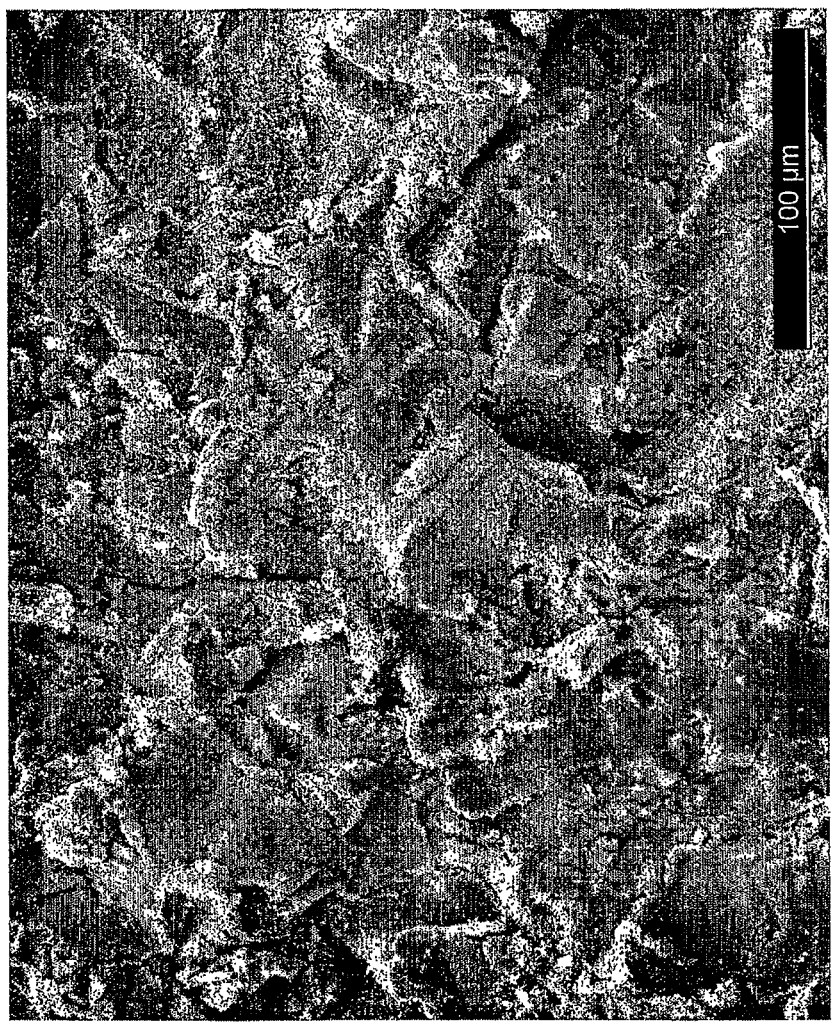
Figure 6:
Figure 7:
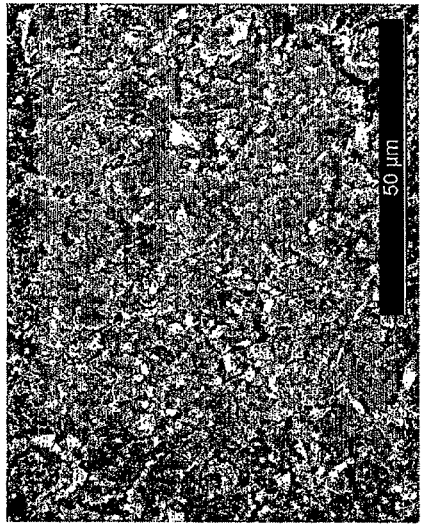
Figure 7:
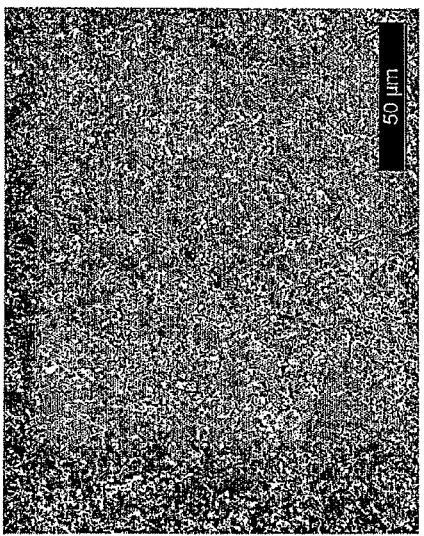
Figure 7:
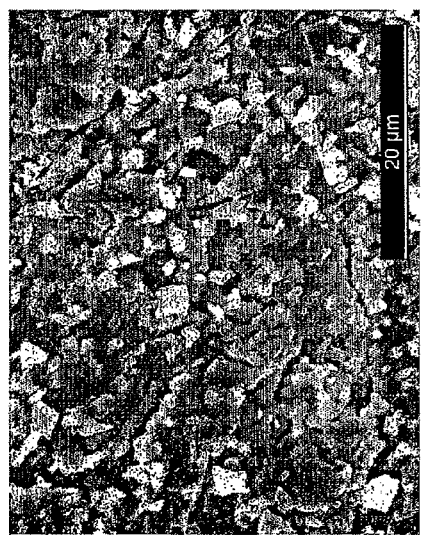
Figure 8:
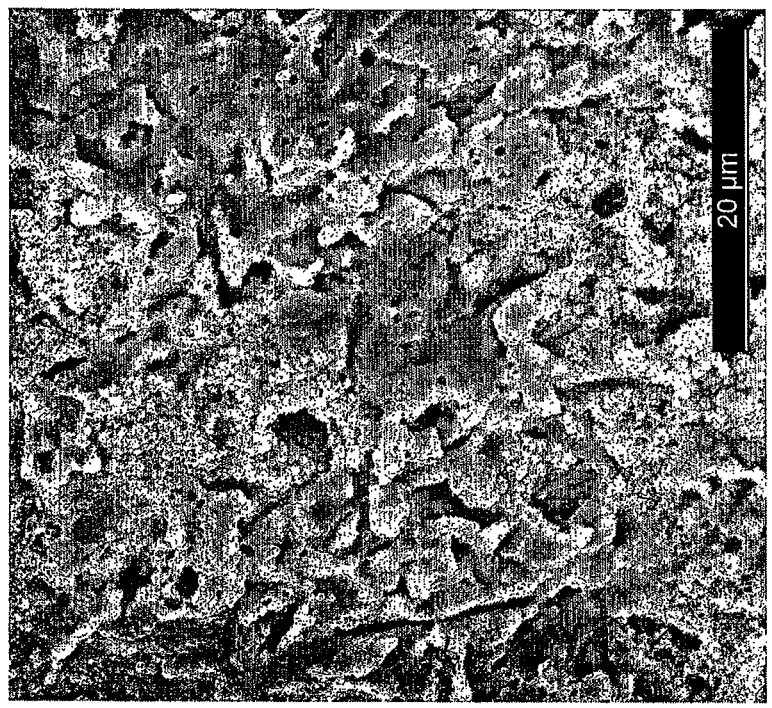
Figure 8:
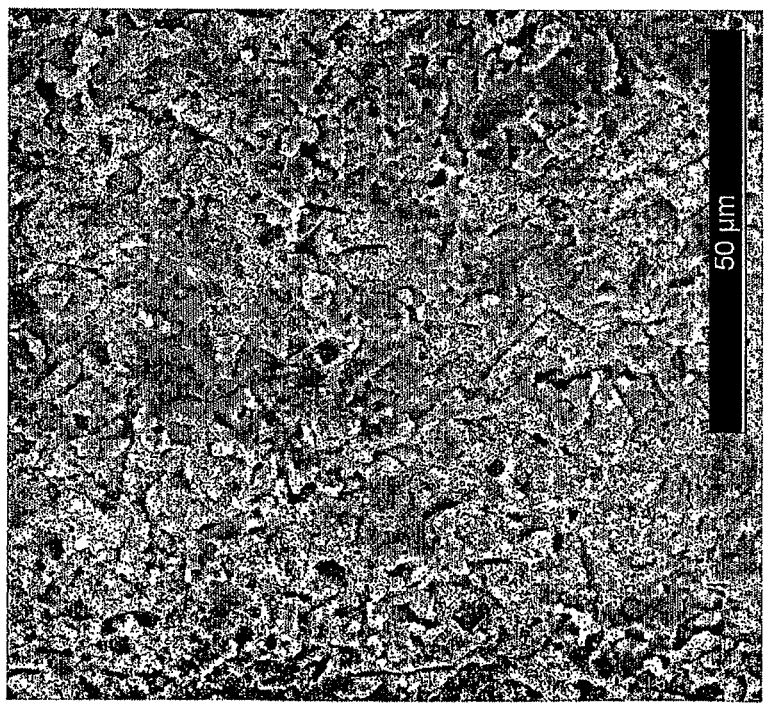
Figure 9:
Figure 9:
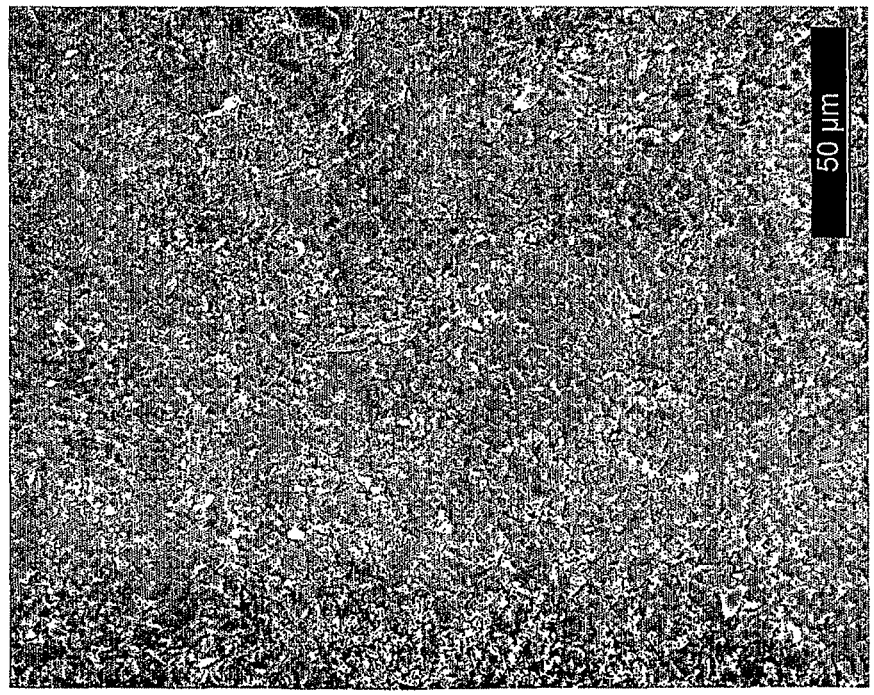
Figure 10:
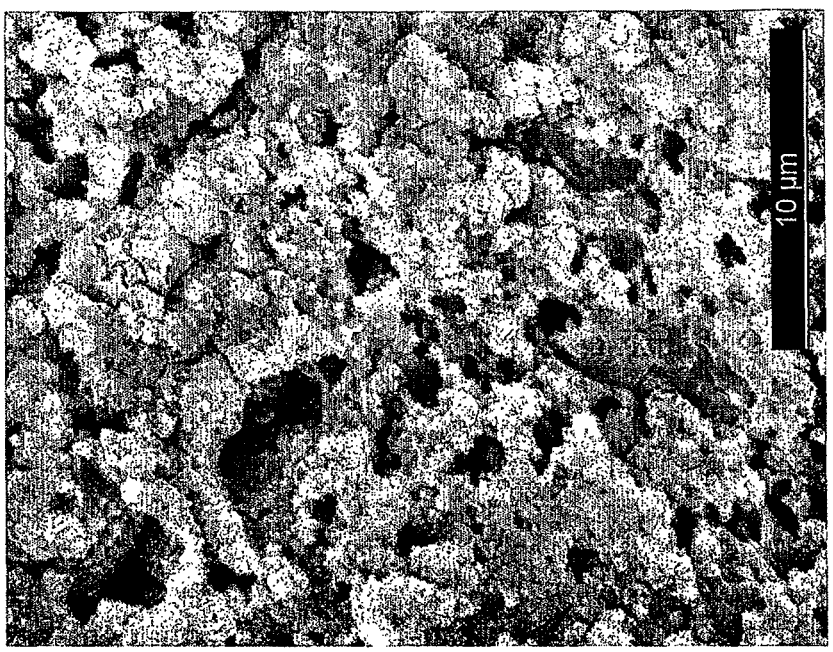
Figure 10:
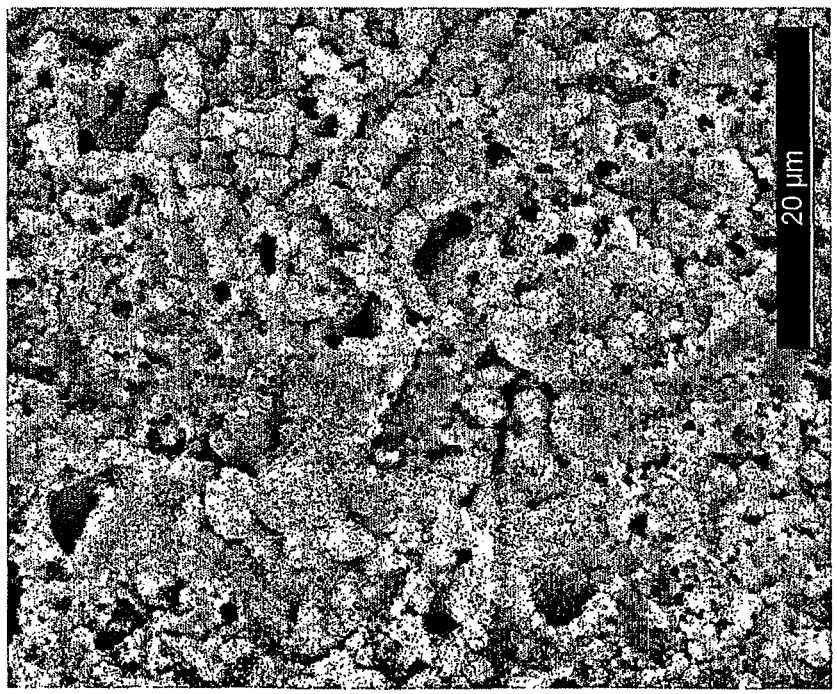
Figure 11:
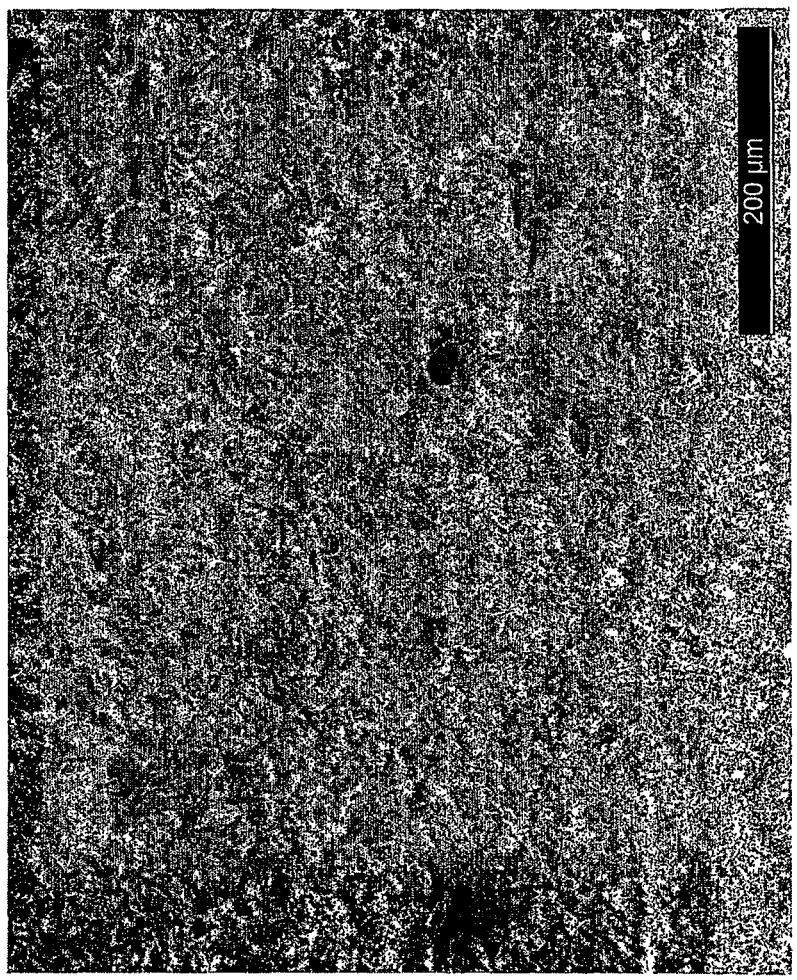

The invention shall be further illustrated below by embodiments in connection with the figures, in which:

FIG. 1-3 show the surface topography of a ceramic implant after injection molding and after blasting with an organic blasting agent prior to sintering in different resolutions;

FIG. 4-6 surface topography of a ceramic implant after injection molding and after blasting with an anorganic blasting agent prior to sintering in different resolutions;

FIG. 7 surface pictures of example 3 in different resolutions prior to etching;

FIG. 8 surface pictures of example 3 in different resolutions after etching;

FIG. 9 surface pictures of example 4 in different resolutions prior to etching;

FIG. 10 surface pictures of example 4 in different resolutions after etching; and FIG. 11 surface picture of a green body after blasting.

DETAILED DESCRIPTION OF THE PREFERRED EMBODIMENTS

The present invention describes the possibility to structure the surface of implants, which especially are produced from ceramic- but also of metallic materials. Aim of the surface modification are a better anchoring of the implants in hard tissue, a better bond between hard tissue and implant surface, a better bond between soft tissue and implant surface, and a better interaction of the implant surface on the interface between implant surface and hard tissue and/or soft tissue.

The production of the zirconium oxide-, titanium oxide- and/or aluminium oxide and/or mixed ceramics for implants, also by the aid of CIM or MIM, is basically known from the state of the art and correspondingly shall not be further discussed. In this context, reference is made to the disclosure of the above mentioned documents.

Preferably, the invention concerns implants which are anchored in the hard- and/or soft tissue and which serve the temporary or permanent replacement or support of accident-, use-, deficiency- or disease-damaged or otherwise degenerated parts of the musculoskeletal system, including the chewing apparatus, especially the dental area with its corresponding, also aesthetic aspects. Hence, for example hip- and knee joint prostheses, spine implants and dental implants have been used clinically for many years. The problem of the improved osteointegration features, or osseointegration features, respectively, is solved according to the invention by a corresponding surface structure or surface treatment, respectively, of the (ceramic-) surface of the implant, wherein the treatment can be carried out over the entire implant surface as well as over partial areas of the implant surface. By way of such a surface structuring, it is ensured that the otherwise bio-inert ceramics, such as preferably zirconium oxide, titanium oxide, or aluminium oxide, or mixtures thereof, can be integrated in the hard- and/or soft tissue.

The structural and functional anchoring, e.g. of a dental implant, in the bone, normally is achieved by applying a macro-roughness, and/or a possibly additional micro-roughness. The macro-roughness can for example be obtained by a mechanical blasting process according to the state of the art, the micro-roughness subsequently for example in an additive process by plasma technique, or in a subtractive process by chemical- or molten salt etching on the surface. The degree of anchoring of the implant in the bone can be determined by mechanical measurements. Numerous tests have shown that the sufficient anchoring of an implant in the bone depends to a great extent on the surface condition of the implant, especially on the roughness at its surface.

The present invention describes a specific and newly created roughness for a preferably enlarged effective surface for a better osteointegration of implants, which are produced of ceramics, preferably of titanium oxide, zirconium oxide, or aluminium oxide, or mixtures thereof. This biologically effective surface according to the invention can be produced by blasting of the green body after casting or injection molding and prior to the final sintering during the CIM or MIM process, respectively, by an additional mechanical subsequent or antecedent chemical treatment, for example etching or similar, or by a combination of such methods.

The surface according to the invention can for example be produced by treating the green body on its surface prior to the final sintering by blasting with different blasting agents, until a corresponding surface structuring results. This for example can be carried out by a defined blasting process.

Furthermore, the possibility exists to apply the blasting agent to the isostatic compression- or casting- or injection molding tool prior to casting or injection molding, or to treat it therewith.

As mentioned, all known abrasive or surface densifying blasting agents are suitable, such as metallic blasting agents, ceramic blasting agents, or natural blasting agents in different particle sizes, depending on the desired roughness or porosity of the surface, respectively. Therein, it is also found that the surfaces produced according to the invention can contain partially incorporated component parts of the blasting agents used. Advantageously, further blasting agents can be used, which can be removed without residues prior to the final sintering. Such suitable blasting agents are for example ice (balls or —particles), organic blasting agents or especially carbamide, melamine resin, biuret, melamine, ammonium carbonate and ammonium bicarbonate. These blasting agents are removed without residues at temperatures up to max. 600° C. prior to the final sintering or preferably prior to a heat treatment prior to the debindering. Therein, it is advantageous to carry out this treatment in an oxidizing or reducing or inert atmosphere. The dimension of the blasting agent(s) determines the dimension of the surface structuring. A mixture of two different agents with two different sizes thus results in "bimodal" structurings with two different structure-dimension-parts, a fine structure and a rough structure.

Series 1

Example 1

A green body in the form of a cylindrical dental implant with a length of 10 mm and a diameter of 4 mm was injection molded from yttrium-stabilized zirconium oxide powder. After injection molding and prior to sintering, the surface was blasted with a mixture of peach- and apricot pits with a particle size of 100-150 µm with a pressure of 0.8 bar for 50 s. The resulting surface was examined by scanning electron microscopy. The surface topography created by the blasting is shown in different resolutions in FIGS. 1, 2, and 3. The macro-roughness thereby produced leads to a good osseointegration of the implant after sintering.

Example 2

A green body in the form of a cylindrical dental implant with a length of 10 mm and a diameter of 4 mm was injection molded from yttrium-stabilized zirconium oxide powder. After the injection molding and prior to sintering, the surface was blasted with aluminium oxide with a particle size of about 250 µm with a pressure of 0.8 bar for 50 s. The resulting surface was examined by scanning electron microscopy. The surface topography created by the blasting is shown in different resolutions in FIGS. 4, 5, and 6. The macro-roughness thereby produced leads to a good osseointegration of the implant after sintering.

Series 2

In a second series of experiments, the green bodies were treated prior to sintering by the use of a blasting agent, which contained two different materials with different particle sizes. Therein, generally the following process management and settings of the parameters are preferred:

Preferred Parameters:

1. passage with ⅔ vol. organic material (peach pits and/or apricot pits in correspondingly ground form) 0.3 to 0.6 mm particle size and ⅓ vol. $Al_2O_3$-220 mesh (about 0.07 mm particle size). Both components are present as a mixture and are blasted simultaneously.

| | |
|---|---|
| Pressure: | 3 bar to 5 bar |
| Exposition-blasting time: | 25 sec to 45 sec |
| Distance, jet to implant: | 25 mm to 80 mm |
| Bore diameter of the jet: | 1.2 mm to 2.0 mm |

2. passage with $Al_2O_3$ mesh 220, thereby more rough residues of the organic agent can be removed.

| | |
|---|---|
| Pressure: | 0.2 bar to 0.4 bar |
| Exposition-blasting time: | 15 sec to 25 sec |
| Distance, jet to implant: | 30 mm to 50 mm |
| Bore diameter of the jet: | 0.8 mm to 1.0 mm |

Especially preferred for the 2. passage are:

| | |
|---|---|
| Pressure: | 0.2 bar |
| Exposition-blasting time: | 20 sec |
| Distance, jet to implant: | 30 mm |
| Bore diameter of the jet: | 1.0 mm |

Generally, the parameters shown below can be selected:

1. passage with ⅔ vol. organic material (peach pits and/or apricot pits in correspondingly ground form) 0.3 to 0.6 mm particle size and ⅓ vol. $Al_2O_3$-220 mesh.

| | |
|---|---|
| Pressure: | 2 bar to 7 bar |
| Exposition-blasting time: | 15 sec to 65 sec |
| Distance, jet to implant: | 25 mm to 80 mm |
| Bore diameter of the jet: | 1.2 mm to 2.0 mm |

2. passage with $Al_2O_3$ mesh 220.

| | |
|---|---|
| Pressure: | 0.2 bar to 0.8 bar |
| Exposition-blasting time: | 10 sec to 35 sec |
| Distance, jet to implant: | 30 mm to 50 mm |
| Bore diameter of the jet: | 0.8 mm to 1.2 mm |

Example 3

A green body in the form of a cylindrical dental implant with a length of 10 mm and a diameter of 4 mm was injection molded from yttrium-stabilized zirconium oxide powder. After the injection molding and prior to sintering, the surface was blasted with a mixture of peach- and apricot pits ⅔ vol. (organic agent) 0.3 to 0.6 mm particle size and ⅓ vol. $Al_2O_3$-220 mesh with a pressure of 3.0 bar for 45 s.

Subsequently, 2. blasting passage with $Al_2O_3$ mesh 220, thereby more rough residues of the organic agent can be removed, with a pressure of 0.8 bar for 50 s.

The resulting surface was examined by scanning electron microscopy. The surface topography created by the blasting is shown in different resolutions in FIG. 7 (*a-c*). The macro-roughness thereby produced leads to a good osseointegration of the implant after sintering.

The values of the roughness measurements of the surface of the implant thus produced in the state prior to etching, measured at the threaded base, result in the following values:

| Measured values in µm | | | | | | |
|---|---|---|---|---|---|---|
| Sa | Sq | St | Sk | Rt | Rq | Ra |
| 1.05 | 1.25 | 6.42 | 3.38 | 8.67 | 1.41 | 1.10 |

Measurement parameters (also used in all further measurements): Gauss filter with cut off=110 µm; field of measurement about 770 µm×770 µm, object lens L20X, Stitchen 1×1;

confocal microscope 3 dimensional measurement method, apparatus: white light microscopy μ-surf.

Subsequently, the implant thus produced was etched in a molten salt, consisting of 50% KOH and 50% LiOH (weight percent) at 200° C. for 30 hours. Thereby, the surface structure was significantly changed, as can be derived from FIG. 8 (a-b).

The values of the roughness measurements of the surface of the implant in the state after etching, measured at the threaded base, result in the following values:

| Measured values in μm | | | | | | | |
|---|---|---|---|---|---|---|---|
| Sa | Sq | St | Sk | Rt | Rq | Ra | |
| 1.12 | 1.41 | 7.57 | 7.87 | 16.81 | 3.91 | 1.23 | after etching |

Example 4

A green body in the form of a cylindrical dental implant with a length of 10 mm and a diameter of 4 mm was injection molded from yttrium-stabilized zirconium oxide powder. After the injection molding and prior to sintering, the surface was blasted with a mixture of peach- and apricot pits ⅔ vol. (organic agent) 0.3 to 0.6 mm particle size and ⅓ vol. $Al_2O_3$±220 mesh with a pressure of 3.0 bar for 25 s.

Subsequently, 2. blasting passage with $Al_2O_3$ mesh 220, thereby more rough residues of the organic agent can be removed, with a pressure of 0.2 bar for 20 s.

The resulting surface was examined by scanning electron microscopy. The surface topography created by the blasting is shown in different resolutions in FIG. 9 (a-b). The macro-roughness thereby produced leads to a good osseointegration of the implant after sintering.

The values of the roughness measurements of the surface of the implant in the state prior to etching, measured at the threaded base, result in the following values:

| Measured values in μm | | | | | | | |
|---|---|---|---|---|---|---|---|
| Sa | Sq | St | Sk | Rt | Rq | Ra | |
| 1.07 | 1.31 | 6.42 | 3.53 | 6.93 | 1.43 | 1.03 | prior to etching |

Subsequently, the implant thus produced was etched in a molten salt, consisting of 50% KOH and 50% LiOH (weight percent) at 200° C. for 30 hours. Thereby, the surface structure was significantly changed, as can be derived from FIG. 10 (a-b).

The values of the roughness measurements of the surface of the implant in the state after etching, measured at the threaded base, result in the following values:

| Measured values in μm | | | | | | | |
|---|---|---|---|---|---|---|---|
| Sa | Sq | St | Sk | Rt | Rq | Ra | |
| 1.95 | 1.53 | 17.39 | 4.17 | 41.11 | 4.58 | 1.80 | after etching |

In FIG. 11, a green body prior to sintering is shown, wherein it can be seen how the organic and anorganic residues of the blasting agent are still present on the surface.

The invention claimed is:

1. A method for the production of a metallic and/or ceramic implant with a structured surface for insertion into hard tissue, such as into a bone, and/or into soft tissue, comprising:
   using a molding process in a mold-tool to form a green body from a starting material, said molding process selected from the group consisting of: cold-isostatic compression, casting and/or injection molding, and
   subsequently sintering the green body to form an implant, wherein prior to sintering, the surface of said green body is changed and/or prepared such that after the sintering a structured surface in the form of a macroporous and/or macro-structured surface is present,
   and wherein said changed and/or prepared surface of said green body is obtained by a blasting modification of an inner surface of said mold-tool with an abrasive and/or surface-densifying blasting agent, prior to said molding process.

2. A method for the production of a metallic and/or ceramic implant with a structured surface for insertion into hard tissue, such as into a bone, and/or into soft tissue, comprising:
   using a molding process in a mould-tool to form a green body from a starting material, said molding process selected from the group consisting of: cold-isostatic compression, casting and/or injection molding, and
   subsequently sintering the green body to form an implant, wherein prior to sintering, the surface of said green body is changed and/or prepared such that after sintering a structured surface in the form of a macroporous and/or macro-structured surface is present,
   and wherein said changed and/or prepared surface of said green body is obtained in that prior to said molding process the inner surface of said mold tool is provided with a high melting organic filler material with a particle size in the range of 0.01-0.25 mm by the use of a binder, such that after molding of the green body, said filler material is incorporated selectively on or in the surface of said green body and is removed during the sintering process to form said structured surface.

3. The method according to claim 1 or 2, wherein after sintering, no additional post-treatment is carried out to form the macroporous and/or macro-structured surface.

4. The method according to claim 1 or 2, wherein the green body is modified after the cold-isostatic compression, casting and/or injection molding and prior to the final sintering by blasting of the surface of the green body.

5. The method according to claim 4, wherein the blasting agent for the blasting is an abrasive and/or surface-densifying metallic blasting agent, a ceramic blasting agent, an organic or natural blasting in various particle- and splitter sizes, or mixtures of said blasting agents.

6. The method according to claim 5, wherein the particle size of the blasting agent is in the range of 0.01-0.25 mm.

7. The method according to claim 4, wherein the blasting agent for the blasting are ice balls, ice particles, or organic blasting agents selected from the group of stearates, waxes, paraffines, carbamide, melamine resin, biuret, melamine, ammonium carbonate, ammonium bicarbonate or mixtures thereof.

8. The method according to claims 7, wherein the blasting agents can be removed without residues at temperatures up to max. 600° C. prior to the final sintering, wherein this removal is carried out in an oxidizing or reducing or inert atmosphere, such as under $O_2$, $N_2$, $NH_4$, Ar, mixtures thereof, or in vacuum.

9. The method according to claim 7, wherein the ammonium bicarbonate sublimes from the surface of the green body at 65° C. and leaves behind the desired structure in the surface.

10. The method according to claims 4, wherein the blasting pressure lies in the range of 0.2-7 bar, and wherein the blasting treatment is carried out during a time period between 15 and 65 seconds, wherein the distance from the jet to the implant is selected in the range of 25-80 mm, at a bore diameter of the jet in the range of 0.8-1.2 mm.

11. The method according to claim 4, wherein a mixture of two different blasting agents with a different particle size is used as a blasting agent, wherein the difference in the average particle size of the different blasting agents lies in the range of a factor 5-10.

12. The method according to claim 11, wherein a first blasting agent is present in the mixture, which has an average particle size in the range of 0.1-0.8 mm, wherein it is an organic blasting agent, and wherein a second blasting agent is present in the mixture, which has an average particle size in the range of 0.01-0.9 mm, wherein it is an anorganic blasting agent, wherein the ratio of the first to the second blasting agent is in the range of 5:1-1:5.

13. The method according to claim 11, wherein the blasting is carried out in two steps, wherein in a first step said mixture is used and in a second step only the blasting agent with the smaller particle size is used, as an anorganic blasting agent, wherein the second step is carried out under an at least 5-10 times lower blasting pressure.

14. The method according to claim 11, wherein in the step of using a mixture a pressure within the range of 2-7 bar is used, and/or the time of treatment is in the range of 15-65 seconds and/or the distance from the jet to the implant is in the range of 25-80 mm, and/or the bore diameter of the jet is in the range of 1.2-2.0 mm, and wherein in a second step a pressure lies in the range of 0.2-0.8 bar, and/or wherein the time of treatment is in the range of 10-35 seconds, and/or wherein the distance from the jet to the implant is in the range of 30-50 mm, and/or the bore diameter of the jet is in the range of 0.8-1.2 mm.

15. The method according to claim 1 or 2, wherein, following the sintering, the porous surface is further modified at least area-wise with an erosive chemical or physical treatment.

16. The method according to claim 15, wherein the subsequent treatment comprises a molten salt modification carried out at least area-wise, wherein the implant is structured by etching on the surface by a molten salt, wherein especially during etching essentially exclusively an erosion of material takes place.

17. The method according to claim 16, wherein the molten salt is a molten salt of alkali- and/or alkaline earth-nitrates, hydroxides or halogens, or a mixture of these salts.

18. The method according to claim 17, wherein the molten salt is a molten salt of potassium hydroxide, and/or sodium hydroxide, and/or lithium hydroxide.

19. The method according to claim 16, wherein the molten salt is a molten salt with at least one hydroxide, especially with at least one alkali- and/or alkaline earth-hydroxide, or wherein the molten salt is a molten salt consisting exclusively of one or more hydroxides.

20. The method according to claim 16, wherein the molten salt is a molten salt with at least one chloride, with at least one alkali- and/or alkaline earth chloride, or wherein the molten salt is a molten salt consisting exclusively of one or more chlorides, of one or more alkali- and/or alkaline earth-chlorides.

21. The method according to claim 16, wherein the molten salt is a binary molten salt of potassium hydroxide and sodium hydroxide, or of potassium chloride and lithium chloride, in a ratio of 2:1-0.5:1, wherein a temperature in the range of 100-600° C. is used.

22. The method according to claim 16, wherein the surface is exposed to a molten salt at least area-wise over a period of 10 minutes to 300 hours.

23. The method according to claim 1 or 2, wherein the implant consists of ceramics.

24. The method according to claim 23, wherein the implant contains zirconium oxide, to which optionally yttrium oxide and hafnium oxide is added, and/or wherein the implant contains aluminum oxide, to which optionally silicium dioxide, ferric (III) oxide, and/or sodium oxide is added, and/or wherein the implant contains silicium nitride, to which optionally silicium dioxide, ferric (III) oxide and/or sodium oxide is added, and/or wherein the implant contains titanium oxide, and/or wherein it is formed of mixtures of said materials.

25. The method according to claim 1, wherein the green body is changed and/or prepared at least on its surface during the cold-isostatic compression, casting and/or injection molding by the addition of a filler material to the starting material prior to sintering.

26. The method according to claim 25, wherein the filler material is selectively only arranged in the surface region, wherein in a first step starting material with filler material is applied to the form, and subsequently in a second step starting material without filler material.

27. The method according to claim 2, wherein the filler material are granularly formed high-melting organic compounds, selected from carbamide, biuret, melamine, melamine resin, ammonium carbonate or ammonium bicarbonate, or mixtures thereof.

28. The method according to claim 1 or 2, wherein the metallic and/or ceramic implant has a structured porous surface.

* * * * *